United States Patent [19]
Mine et al.

[11] Patent Number: 6,002,042
[45] Date of Patent: Dec. 14, 1999

[54] LIQUID CRYSTAL COMPOUND

[75] Inventors: Takakiyo Mine; Tomoyuki Yui; Masahiro Johno; Yuki Motoyama; Hiroshi Mineta, all of Tsukuba, Japan

[73] Assignee: Mitsubishi Gas Chemical Company, Inc., Tokyo, Japan

[21] Appl. No.: 09/006,384

[22] Filed: Jan. 13, 1998

[30] Foreign Application Priority Data

| Jan. 14, 1997 | [JP] | Japan | 9-004558 |
| Jan. 16, 1997 | [JP] | Japan | 9-005534 |
| Jul. 10, 1997 | [JP] | Japan | 9-185248 |

[51] Int. Cl.$^6$ ................................ C07C 69/76
[52] U.S. Cl. .................................. 560/66
[58] Field of Search ........................... 560/66

[56] References Cited

FOREIGN PATENT DOCUMENTS

| 0418140 | 3/1991 | European Pat. Off. . |
| 643154 | 1/1989 | Japan . |
| 1213390 | 8/1989 | Japan . |
| 1316339 | 12/1989 | Japan . |
| 1316367 | 12/1989 | Japan . |
| 1316372 | 12/1989 | Japan . |
| 2-28128 | 1/1990 | Japan . |
| 2225434 | 9/1990 | Japan . |
| 2229128 | 9/1990 | Japan . |
| 3292388 | 12/1991 | Japan . |

OTHER PUBLICATIONS

A.D.L. Chandani, et al., "Tristable Switching in Surface Stabilized Ferroelectric Liquid Crystals with a Large Spontaneous Polarization", Japan Journal of Appl. Physics, 27(5), L729–L732 (May 1988).

A.D.L. Chandani, et al., "Novel Phases Exhibiting Tristable Switching", Japan Journal of Appl. Physics, 28(7), L1261–L1264 (Jul. 1989).

A.D.L. Chandani, et al., "Antiferroelectric Chiral Smectic Phases Responsible for the Tristable Switching in MHPOBC", Japan Journal of Appl. Physics, 28(7), L1265–L1268 (Jul. 1989).

M. Johno, et al. "Smectic Layer Switching by an Electric Field in Ferroelectric Liquid Crystal Cells", Jap. Jour. Appl. Phys. 28(1), L119–L120 (Jan. 1989).

M. Johno, et al., Correspondence between Smectic Layer Switching and DC Hysteresis of Apparent Tilt Angle in an Antiferroelectric Liquid Crystal Mixture, Jap. Jour. Appl. Phys., 29(1), L111–L114 (Jan. 1990).

Y. Suzuki, et al., "New Fluorine–containing Ferroelectric Liquid Crystal Compounds Showing Tristable Switching", Liquid Crystals, 6(2), 167–174 (1989).

E. Gorecka, et al., "Molecular Orientational Structures in Ferrolectric, Ferrielectric and Antiferroelectric Smectic Liquid Crystal Phases as Studied by Conoscope Observation", Jap. Journal of Appl. Physics, 29(1), 131–137 (Jan. 1990).

Y. Suzuki, et al, "New Flourine–Containing Ferroelectric Liquid Crystal Compounds Showing Tristable Switching", Liquid Crystals, 1989, vol. 6, No. 2, pp. 167–174.

C.J. Booth, et al, "The Ferro–, Ferri–and Antiferro–electric Properties of a Series of Novel 2–or 3–Substituted–Alkyl 4–(4'–dodecyloxybiphenyl–4–carbonyloxy)–Benzoate Esters", Liquid Crystals, 1996, vol. 20, No. 6, pp. 815–823.

K. Mikami, et al, "Diastereotropic Phenomena for the Appearance of SmCA* Phase in α–Trifluoromethyl–β–Methyl–Substituted Liquid Crystalline Molecules", Chemistry Letters 1996, pp. 861–862.

K. Mikami, et al, "Binaphthol–Titanium Complex–Catalyzed Fluoral–Ene Reaction with Vinyl Sulfides for Asymmetric Synthesis of Diastereomeric α–Trifluoromethyl–β–Methyl Carbinols: Diastereomer Switch of Anti–ferroelectric or Ferroelectric Properties of Diastereomeric Liquid–Crystalline Systems", Synlett, Sep. 1996, pp. 837–838.

Primary Examiner—Paul J. Killos
Attorney, Agent, or Firm—Sherman and Shalloway

[57] ABSTRACT

A liquid crystal compound represented by the following general formula (1):

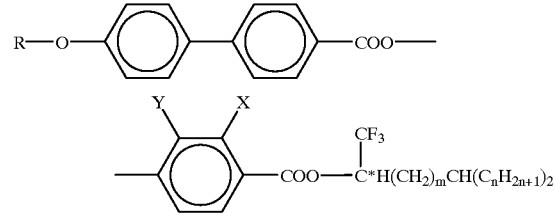

(1)

wherein R is a linear alkyl group having 6 to 12 carbon atoms, X and Y are both a hydrogen atom, or one of them is a hydrogen atom and the other is a fluorine atom, m is an integer of 0 to 5, n is an integer of 1 to 5, and C* is an asymmetric carbon atom. Since the liquid crystal compounds of the present invention have an anti-ferroelectric phase or a ferrielectric phase and the anti-ferroelectric phase or a ferrielectric phase has a highly practical phase sequence and wide temperature range, they are of great industrial value.

7 Claims, 1 Drawing Sheet

- ⊙ : UP STATE ON THE PLANE
- ⊗ : DOWN STATE ON THE PLANE

LIQUID CRYSTAL COMPOUND

FIELD OF THE INVENTION

This invention relates to a novel liquid crystal compound having an optically active group, mainly to a liquid crystal compound which can be advantageously used as an anti-ferroelectric liquid crystal or ferrielectric liquid crystal according to the type of the optically active group.

PRIOR ART

Liquid crystal display devices (LCD) are being widely used mainly in portable equipment as flat panel displays substituting conventional cathode ray tubes (CRT). Along with recent increases in the number of functions of personal computers and word processors and the volume of information to be processed, there has been growing demand for LCDs having advanced functions, that is, larger display capacity, full color display ability, wide viewing angle, high-speed response and high contract.

However, so long as a nematic liquid crystal available at present is used in a display device, even an active matrix driven liquid crystal display device (AM) used in a liquid crystal television set has found it not easy to increase its size and decrease its production cost due to its complicated production process and low yield. Further, in a simple matrix driven STN liquid crystal display device (STN), the driving of a large-capacity display device is not always easy and its response time is limited and hence, video frame rate display is difficult to obtain. At present, therefore, it cannot at all be said that the nematic liquid crystal display device can satisfy requirements for the above high-function large-sized liquid crystal display device.

As for display quality, further, TFT and STN display devices using a nematic liquid crystal compound have such a key problem as a narrow viewing angle. Though various solutions have been proposed, it is difficult to find out a radical solution so long as a nematic liquid crystal compound is used.

Under the circumstances, a liquid crystal display device produced using a ferroelectric liquid crystal compound is attracting attention as a liquid crystal display device with a fast response and a wide viewing angle. A surface-stabilized ferroelectric liquid crystal (SSFLC) device disclosed by Clark and Lagerwall has come under notice in that it has a fast response and a wide viewing angle which have not been achieved in the past. Its switching characteristics have been studied in detail, and a number of ferroelectric liquid crystal compounds have been synthesized for optimizing various physical property constants.

When a ferroelectric liquid crystal is used as a liquid crystal display device, however, the alignment of its liquid crystal molecules must be devised to achieve a practically acceptable contrast because its threshold characteristic is insufficient and its layer has a chevron structure. Further, since the alignment of its liquid crystal molecules is difficult to control, it is not easy to attain bistability, which is one of the most important characteristics of SSFLC, with good reproducibility. Further, there is another problem that when the alignment is destroyed by a mechanical shock, it is difficult to restore the alignment. Therefore, these problems must be overcome to put the device to practical use.

As described above, efforts have been made in various ways to develop novel modes for increasing the size and resolution of a liquid crystal display device. Under the circumstances, the development of devices having a switching function which are completely different from the prior art devices is also under way.

Switching among tristable states in an anti-ferroelectric phase of a liquid crystal compound having an anti-ferroelectric phase is one of these new switching mechanisms. (Japanese Journal of Applied Physics, Vol. 27, pp. L729, 1988).

The anti-ferroelectric liquid crystal device (or the liquid crystal using an anti-ferroelectric phase) has three stable states, i.e., two uniform states (Ur, Ul) observed in a ferroelectric liquid crystal device and a third state. Chandani et al report that the above third state is an anti-ferroelectric phase (Japanese Journal of Applied Physics, Vol. 28, pp. L1261, 1989, Japanese Journal of Applied Physics, Vol. 28, pp. L1265, 1989).

The above switching among three stable states is the first characteristic of an anti-ferroelectric liquid crystal device.

The second characteristic of the anti-ferroelectric liquid crystal device is that a sharp threshold value exists with respect to an applied voltage. Further, the anti-ferroelectric liquid crystal device has a memory effect, which is the third characteristic of the anti-ferroelectric liquid crystal device.

Making use of the above excellent characteristics, a liquid crystal display device having a fast response and a good contrast can be realized. Another major characteristic of the anti-ferroelectric liquid crystal is that its layer structure is easily switched when an electric field is applied (Japanese Journal of Applied Physics, Vol. 28, pp. L119, 1989, Japanese Journal of Applied Physics, Vol. 29, pp. L111, 1990).

On the basis of the above characteristics, a liquid crystal display device almost free of defects and capable of self-restoring the alignment of its molecules can be produced, and a liquid crystal device having an excellent contrast can be achieved.

As an anti-ferroelectric liquid crystal compound, there are known compounds disclosed in JP-A-1-213390, JP-A-1-316339, JP-A-1-316367, JP-A-1-316372, JP-A-2-28218 and "LiquidCrystals", Vol. 6, pp. 167(1989) (the term "JP-A" as used herein means an "unexamined published Japanese patent application"). The number of anti-ferroelectric liquid crystal compounds which have been so far known is not so large as that of ferroelectric liquid crystal compounds, while anti-ferroelectric liquid crystal compounds are increasing in number with advance in studies thereof.

In the field of ferroelectric liquid crystal compounds, attempts are being energetically made to synthesize ferroelectric liquid crystal compounds from the following optically active alcohols in which a fluoroalkyl group is substituted on an asymmetric carbon as an optically active group (e.g., JP-A-64-3154, JP-A-1-316339, JP-A-1-316367, JP-A-1-316372, JP-A-2-225434 and JP-A-2-229128).

  (1)

  (2)

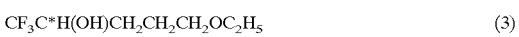  (3)

  (4)

  (5)

  (6)

All of ferroelectric liquid crystal compounds derived from the above optically active alcohols give high spontaneous polarization and also give a relatively fast response since a fluoroalkyl group having a high electronegativity is substituted on the asymmetric carbon atom. Further, it is also known that liquid crystal compounds derived from the above alcohols (4), (5) and (6) easily give liquid crystal compounds having an anti-ferroelectric liquid crystal phase or a ferrielectric phase.

In view of practical use, the number of anti-ferroelectric liquid crystal compounds is still insufficient and a new liquid crystal compound has been desired.

In 4-(1-methylheptyloxycarbonyl)phenyl=4-(4'-octyloxybiphenyl)carboxylate (to be abbreviated as "MHPOBC" hereinafter) which is an anti-ferroelectric liquid crystal compound, a ferrielectric phase (SCγ* phase) was found in 1989 for the first time (Japanese Journal of Applied Physics, Vol. 29, No. 1, 1990, pp. L131–137). The structural formula and phase transition temperature (° C.) of this MHPOBC are shown below.

Structural formula:

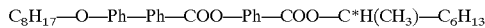
$C_8H_{17}$—O—Ph—Ph—COO—Ph—COO—C*H(CH$_3$)—C$_6$H$_{13}$ (wherein Ph is a 1,4-phenylene group and C* is an asymmetric carbon atom.)

Phase sequence:

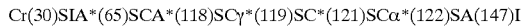
Cr(30)SIA*(65)SCA*(118)SCγ*(119)SC*(121)SCα*(122)SA(147)I

[wherein Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase and I is an isotropic phase.]

The ferrielectric phase will be explained with reference to FIGS. 1 and 2.

Figure 1:
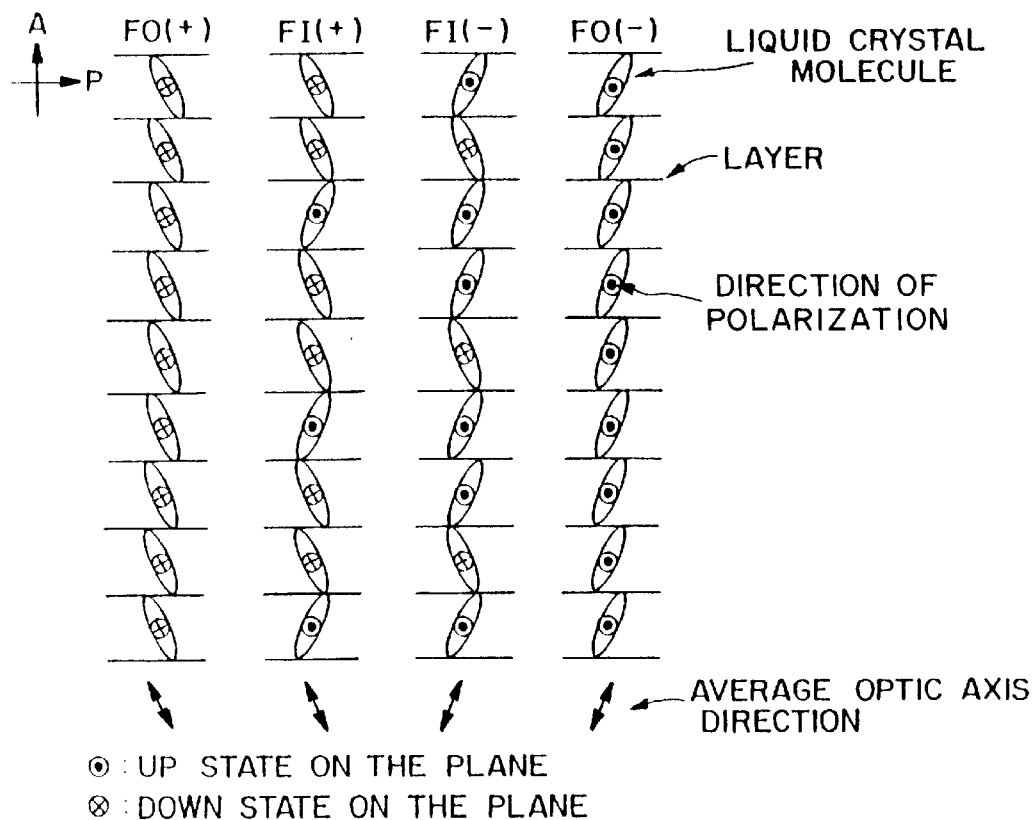
FIG. 1 is a diagram showing the molecular arrangement of a ferrielectric phase. FI(+) and FI(-) indicate a ferrielectric state and FO(+) and FO(-) indicate a ferroelectric state.

The ferrielectric phase has the molecular orientation state of FI(+) (when an applied voltage is positive) or FI(-) (when an applied voltage is negative) of FIG. 1. In a state in which no electric field is applied, FI(+) and FI(-) are assumed to be co-present since they are equivalent in molecular orientation to each other.

Therefore, average optic axes are in a direction of a layer normal, and the state free of an electric field is a dark state under the condition of polarizers shown in FIG. 1. This state corresponds to a portion where the intensity of transmitted light is 0 at a voltage of 0 in FIG. 2.

Each of FI(+) and FI(-) has spontaneous polarization as is clearly shown by the molecular orientation state but the spontaneous polarizations are canceled in a state where these are co-present. As a result, an average spontaneous polarization is zero. This shows that a ferrielectric phase is free of an image sticking phenomenon found in a ferroelectric phase, like an anti-ferroelectric phase.

When a voltage applied to a ferrielectric phase is increased, one domain having an extinguished position appears at a voltage lower than that for attaining a ferroelectric state. This shows that the above domain has an optic axis in the direction inclined from the direction of a layer normal although the inclination is not so large as that in a ferroelectric state.

This intermediate state is considered to be FI(+) or FI(-). In this case, a change in the intensity of transmitted light to be observed between a voltage of 0 V and a voltage of 4 V in FIG. 2 should be not continuous but stepwise. In FIG. 2, however, a continuous change in the intensity of transmitted light is observed. This is presumably because the threshold voltage for a change from FI(+) to FO(+) or from FI(-) to FO(-) is not sharp.

As for a liquid crystal compound of the present invention, a liquid crystal phase in which the above-described intermediate state is always observed is called "ferrielectric phase" and a liquid crystal compound in which the ferrielectric phase is the widest in the phase sequence is called "ferrielectric liquid crystal compound".

When an applied voltage is further increased, the phase is transited to an ferroelectric phase FO(+) or FO(-) which is a stable state in accordance with the direction of an electric field. That is, a portion in which the intensity of transmitted light is brought into a saturated state (flat portions on left and right sides) in FIG. 2 is FO(+) or FO(-).

It is seen from FIG. 1 that, in this ferroelectric state FO(+) or FO(-), spontaneous polarization larger than that in the ferroelectric state FI(+) or FI(-) is developed.

As explained above, in the ferrielectric phase, a state where FI(+) and FI(-) are co-present is used as dark and ferrielectric states FO(+) and FO(-) are used as light.

A conventional ferroelectric phase uses switching between two states of FO(+) and FO(-), but the ferrielectric phase has a major characteristic in switching among four states of FO(+), FI(+), FI(-) and FO(-).

These display principles based on liquid crystal phases utilize the birefringence of a liquid crystal, and when the ferrielectric phase is used, a display device having less dependency upon viewing angle can be produced.

Figure 2:
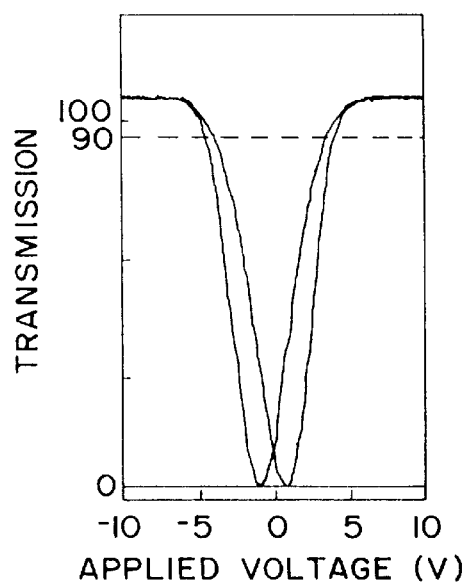
FIG. 2 is a diagram showing an optical response to a triangle wave voltage in a ferrielectric phase.

As shown in FIG. 2, the ferrielectric phase generally shows a small difference between a voltage for a change from a ferrielectric state to a ferroelectric state and a voltage for a change from a ferroelectric state to a ferrielectric state. That is, the ferrielectric liquid crystal has a strong tendency that the width of its hysteresis is very narrow, shows a V-shaped optical response, and has properties suitable for AM driving and gray-scaling display in AM driving.

Further, in the ferrielectric phase, the voltage required for a change in phases between a ferrielectric state and a ferroelectric state (to be referred to as an "phase switching voltage" hereinafter) tends to be much lower than that in an anti-ferroelectric phase, and it can be said from this point that the ferrielectric phase is suitable for AM driving.

However, the number of ferrielectric liquid crystal compounds synthesized so far is extremely small and no ferrielectric liquid crystal compounds which are satisfactory in terms of hysteresis and phase switching voltage have been found in conventionally known ones when application to an AM drive device is taken into consideration.

The present invention has been made from this point of view. It has been found that a biphenyl ester-containing liquid crystal compound derived from a novel optically active alcohol having a trifluoromethyl group on an asymmetric carbon atom and a branched alkyl group having the same chain length at a terminal gives a liquid crystal compound having an anti-ferroelectric phase or ferrielectric phase in a broad temperature range. Thus, the present invention has been accomplished based on this finding.

According to the present invention, there is provided a liquid crystal compound represented by the following general formula (1):

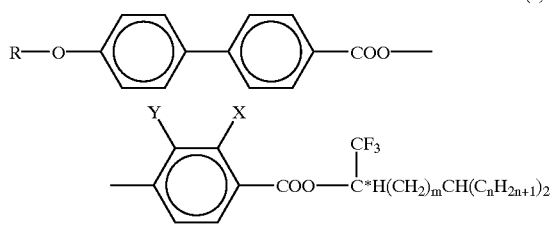

wherein R is a linear alkyl group having 6 to 12 carbon atoms, X and Y are both a hydrogen atom, or one of them is a hydrogen atom and the other is a fluorine atom, m is an integer of 0 to 5, n is an integer of 1 to 5, and C* is an asymmetric carbon atom.

In the above general formula (1) of the present invention, m is an integer of 0 to 5, preferably 0 to 4, and n is an integer of 1 to 5, preferably 1 to 3. There is a tendency that an anti-ferroelectric liquid crystal compound having the widest anti-ferroelectric phase in the liquid crystal phase sequence is given when m is 1 or 3 in the above general formula (1) and a ferrielectric liquid crystal compound having the widest ferrielectric phase in the liquid crystal phase sequence is given when m is 2 in the above general formula (1). This tendency is not clearly defined by the value of m but may be changed by the types of other groups and substituent groups.

Anti-ferroelectric liquid crystal compounds out of the liquid crystal compounds of the present invention can be advantageously used alone or in combination of two or more as a base material for an anti-ferroelectric liquid crystal composition or an additive for modifying an anti-ferroelectric liquid crystal composition. The anti-ferroelectric liquid crystal composition can be advantageously used in a simple matrix liquid crystal display device in particular.

Ferrielectric liquid crystal compounds out of the liquid crystal compounds of the present invention can be advantageously used alone or in combination of two or more as a base material for a ferrielectric liquid crystal composition or an additive for modifying a ferrielectric liquid crystal composition. The ferrielectric liquid crystal composition is held between substrates having nonlinear active devices such as thin film transistors or diodes for each pixel to form an active matrix liquid crystal display device.

The optically active alcohol used in the present invention can be easily produced by a method which the present inventors have proposed and applied for a patent (U.S. patent application Ser. No. 08/968,476 filed on Nov. 12, 1997 and European Patent Application No. 97119821.3 field on Nov. 12, 1997).

The typical production method of the alcohol will be outlined as follows when m is 2 and n is 2.
(a) $Br(CH_2)_2CH(C_2H_5)_2+Mg \rightarrow MgBr(CH_2)_2CH(C_2H_5)_2$
(b) $(a)+CF_3COOH \rightarrow CF_3CO(CH_2)_2CH(C_2H_5)_2$
(c) $(b)+(LiAlH_4) \rightarrow CF_3CH(OH)(CH_2)_2CH(C_2H_5)_2$
(d) $(c)+(CH_3CO)_2O \rightarrow CF_3CH(OCOCH_3)(CH_2)_2CH(C_2H_5)_2$
(e) $(d)+(lipase) \rightarrow R\text{-}(+)CF_3C^*H(OH)(CH_2)_2CH(C_2H_5)_2+S\text{-}(-)CF_3C^*H(OCOCH_3)(CH_2)_2CH(C_2H_5)_2$ The above reaction scheme will be briefly explained as follows.

(a) shows the preparation of a Grignard reagent.
(b) shows a carbon-propagation reaction based on a reaction between the Grignard reagent and trifluoroacetic acid.
(c) shows the reduction of a ketone.
(d) shows the acetylation of a racemic alcohol with anhydrous acetic acid.
(e) shows the hydrolysis of an acetate with lipase (such as lipase MY) for optical resolution.

The intended optically active alcohol of R-configuration and acetate of S-configuration can be obtained from this reaction. An optically active alcohol of S-configuration can be obtained by the hydrolysis of this acetate of S-configuration.

The liquid crystal compound of the present invention can be easily produced using the above optically active alcohol in accordance with a method which the present inventors already proposed (JP-A-3-292388), for example.

The production method will be outlined as follows when m is 2 and n is 2.
(i) $AcO\text{—}Ph(X)\text{—}COOH+SOCl_2 \rightarrow AcO\text{—}Ph(X)\text{—}COCl$
(ii) $(i)+CF_3C^*H(OH)(CH_2)_2CH(C_2H_5)_2 \rightarrow AcO\text{—}Ph(X)\text{—}COO\text{—}C^*H(CF_3)(CH_2)_2CH(C_2H_5)_2$
(iii) $(ii)+Ph\text{—}CH_2NH_2 \rightarrow HO\text{—}Ph(X)\text{—}COO\text{—}C^*H(CF_3)(CH_2)_2CH(C_2H_5)_2$
(iv) $R\text{—}O\text{—}Ph\text{—}Ph\text{—}COOH+SOCl_2 \rightarrow R\text{—}O\text{—}Ph\text{—}Ph\text{—}COCl$
(v) (iii)+(iv)→liquid crystal compound as end product
(wherein Ac is an acetyl group, —Ph(X)— is a 1,4-phenylene group which may have a substituted fluorine atom on the 3-position, Ph— is a phenyl group, —Ph— is a 1,4-phenylene group, R is a linear alkyl group having 6 to 12 carbon atoms, and C* is an asymmetric carbon atom.)

The above production method will be briefly explained as follows.

(i) shows the chlorination of p-acetoxybenzoic acid with thionyl chloride.
(ii) shows the formation of an ester by a reaction between the chloride (i) and the optically active alcohol.
(iii) shows the deacetylation of the ester (ii).
(iv) shows the chlorination of 4'-alkyloxybiphenyl-4-carboxylic acid.
(v) shows the production of a liquid crystal compound by a reaction between the phenol (iii) and the chloride (iv).

The present invention can provide liquid crystal compounds having a novel structure. The liquid crystal compounds provided by the present invention have an anti-ferroelectric phase or ferrielectric phase in the widest range in the liquid crystal phase sequence, and hence, can be said to be an anti-ferroelectric liquid crystal compound. The anti-ferroelectric phase or the ferrielectric phase has a practical wide temperature range and a low melting point and is of great value as a main component of a liquid crystal device material or a component of a liquid crystal composition.

Further, by the studies of the liquid crystal phase sequences of liquid crystal compounds of the present invention, it has been found that the liquid crystal compounds of the invention include ones having unique properties. For example, as is seen from Examples which will be described later, ferrielectric liquid crystal compounds (Examples 1, 3, 12, 19 and 23) having only a ferrielectric phase and anti-ferroelectric liquid crystal compounds (Examples 2 and 21) having only an anti-ferroelectric phase in the liquid crystal phase sequences are included.

Such liquid crystal compounds having only an anti-ferroelectric phase or ferrielectric phase and not other liquid crystal phases are unique and can be expected to be used as a new material.

EXAMPLES

The following examples are provided for the purpose of further illustrating the present invention but are in no way to be taken as limiting.

Example 1

(preparation of R-(+)-3-fluoro-4-(1-trifluoromethyl-4-methyl-pentyloxycarbonyl)phenyl=4'-n-nonyloxybiphenyl-4-carboxylate: R=$C_9H_{19}$, X=H, Y=F, m=2, n=1 in the formula (1))

(1) Preparation of 4-(4'-n-nonyloxy)biphenylcarboxylic acid 10.0 Grams of 4-(4'-hydroxy)biphenylcarboxylic acid and 14.0 g of n-octyl bromide were added to a mixture containing 1,500 ml (milliliters) of ethanol and 200 ml of water, and the mixture was reacted under reflux for 10 hours. 500 Milliliters of water was further added thereto, and the mixture was stirred for 3 hours. After completion of the reaction, the reaction mixture was acidified by adding concentrated hydrochloric acid, 500 ml of the solvent was distilled off, and the residue was cooled to room temperature to give a white solid.

The white solid was fully washed with water and then re-crystallized from chloroform to give 11.0 g of an intended product in the form of a white crystal.

(2) Preparation of 2-fluoro-4-acetoxybenzoic acid 4.3 Grams of 2-fluoro-4-hydroxybenzoic acid and 8.4 g of anhydrous acetic acid were placed in a two-necked flask, and mixed. While the mixture was cooled with water, 5 drops of sulfuric acid were added. After heat generation terminated, the mixture was heated at 80° C. for 30 minutes. Then, the reaction mixture was poured into cold water, and a precipitated crystal was recovered by filtration. The crystal was vacuum-dried and used in the next step. The yield of the crystal was 4.7 g.

(3) Preparation of R-(+)-2-fluoro-4-acetoxy-1-(1-trifluoromethyl-4-methyl-pentyloxycarbonyl)benzene 1.0 Gram of 2-fluoro-4-acetoxybenzoic acid was added to 7 ml of thionyl chloride, and the mixture was reacted under reflux for 5 hours. Then, excessive thionyl chloride was distilled off, and then a mixture containing 1 ml of pyridine, 4 ml of dry ether and 0.6 g of R-(+)-1,1,1-trifluoro-2-hydroxy-5-methyl-hexane was dropwise added. After the dropwise addition, the mixture was stirred at room temperature for 24 hours and diluted with 200 ml of ether, and an organic layer was consecutively washed with diluted hydrochloric acid, with a 1N sodium hydroxide aqueous solution and with water, and dried over magnesium sulfate.

The solvent was distilled off, and the residue was purified by silica gel column chromatography using hexane/ethyl acetate as a solvent, to give 1.1 g of an end product.

(4) Preparation of R-(+)-2-fluoro-4-hydroxy-1-(1-trifluoromethyl-4-methyl-pentyloxycarbonyl)benzene 1.0 Gram of the compound obtained in (3) above was dissolved in 30 ml of ethanol, and 3 g of benzylamine was dropwise added. Further, the mixture was stirred at room temperature for 24 hours, then diluted with 300 ml of ether, consecutively washed with diluted hydrochloric acid and with water, and dried over magnesium sulfate.

The solvent was distilled off, and the residue was subjected to silica gel column chromatography for separation and purification, to give 0.5 g of an end product.

(5) Preparation of R-(+)-3-fluoro-4-(1-trifluoromethyl-4-methyl-pentyloxycarbonyl)phenyl=4'-n-nonyloxybiphenyl-4-carboxylate 10 Milliliters of thionyl chloride was added to 1.0 g of the compound obtained in (1) above, and the mixture was heated under reflux for 10 hours. After excessive thionyl chloride was distilled off, 10 ml of pyridine and 25 ml of toluene were added, and 25 ml of a benzene solution containing 0.5 g of the compound obtained in (4) above was dropwise added to carry out a reaction at room temperature for 10 hours.

After the reaction, the reaction product was diluted with 300 ml of ether and consecutively washed with diluted hydrochloric acid, with a 1N sodium carbonate aqueous solution and with water, and an organic layer was dried over magnesium sulfate. Thereafter, the solvent was distilled off, and the residue was subjected to silica gel chromatography for separation and then re-crystallized from ethanol, to give 0.7 g of an end product.

Examples 2 to 23

End products represented by the general formula (1) in which R, X, Y, m and n are shown in Table 2 were produced in the same manner as in Example 1 except that R-(+)-1,1,1,-trifluoro-2-hydroxy-3-ethyl-pentane (m=0, n=2), R-(+)-1,1,1,-trifluoro-2-hydroxy-3-propyl-hexane (m=0, n=3), R-(+)-1,1,1,-trifluoro-2-hydroxy-4-methyl-pentane (m=1, n=1), R-(+)-1,1,1,-trifluoro-2-hydroxy-4-ethyl-hexane (m=1, n=2), R-(+)-1,1,1,-trifluoro-2-hydroxy-4-propyl-heptane (m=1, n=3), R-(+)-1,1,1,-trifluoro-2-hydroxy-5-ethyl-heptane (m=2, n=2), R-(+)-1,1,1,-trifluoro-2-hydroxy-6-methyl-heptane (m=3, n=1), R-(+)-1,1,1,-trifluoro-2-hydroxy-6-ethyl-octane (m=3, n=2), R-(+)-1,1,1,-trifluoro-2-hydroxy-7-methyl-octane (m=4, n=1) and R-(+)-1,1,1,-trifluoro-2-hydroxy-7-ethyl-nonane (m=4, n=2) were used in place of R-(+)-1,1,1,-trifluoro-2-hydroxy-5-methyl-hexane (m=2, n=1); 4-(4'-hexyloxybiphenyl)carboxylic acid, 4-(4'-heptyloxybiphenyl)carboxylic acid, 4-(4'-octyloxybiphenyl)carboxylic acid, 4-(4'-decyloxybiphenyl) carboxylic acid, 4-(4'-undecyloxybiphenyl)carboxylic acid and 4-(4'-dodecyloxybiphenyl)carboxylic acid were used in place of 4-(4'-nonyloxybiphenyl)carboxylic acid; and p-hydroxybenzoic acid and 3-fluoro-4-hydroxybenzoic acid were used in place of 2-fluoro-4-hydroxybenzoic acid, respectively.

The 1H-NMR spectral data and formula of the end products obtained in the above Examples 1 to 23 are shown in Table 1 and formula (A) below.

The identification results of the liquid crystal phases of the end products are shown In Table 2.

The identification of each liquid crystal phase was carried out by the observation of its texture and conoscopic image and DSC (differential scanning calorimeter). The observation of a conoscopic image is effective for the identification of a ferrielectric phase. The observation of a conoscopic image was carried out in accordance with a literature (Japanese Applied Physics, Vol. 31 pp. 793, 1992).

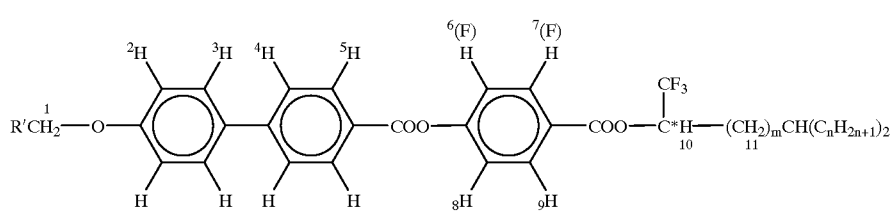

(A)

wherein R' is a linear alkyl group having 5 to 11 carbon atoms, and m and n are the same as defined in the above general formula (1).

TABLE 1

1H-NMR spectral data of the compounds of Examples 1 to 23 (δ(ppm))

| Numerals in formula (A) | 1 | 2 | 3 | 4 | 5 | 6 | 7 | 8 | 9 | 10 | 11 |
|---|---|---|---|---|---|---|---|---|---|---|---|
| Examples 1–3 | 4.0 | 7.0 | 7.6 | 7.7 | 8.2 | 7.2 | — | 7.2 | 8.1 | 5.6 | — |
| Example 4 | 4.0 | 7.0 | 7.6 | 7.7 | 8.2 | 7.2 | — | 7.2 | 8.1 | 5.7 | 1.5 |
| Example 5 | 4.0 | 7.0 | 7.6 | 7.7 | 8.2 | 7.2 | — | 7.2 | 8.0 | 5.6 | 1.8 |
| Example 6 | 4.0 | 7.0 | 7.6 | 7.7 | 8.2 | 7.4 | 8.2 | 7.4 | 8.2 | 5.6 | 1.8 |
| Example 7 | 4.0 | 7.0 | 7.6 | 7.7 | 8.2 | 7.2 | — | 7.2 | 8.0 | 5.6 | 1.8 |
| Example 8–13 | 4.0 | 7.0 | 7.6 | 7.7 | 8.2 | 7.2 | — | 7.2 | 8.1 | 5.6 | 1.8 |
| Example 14 | 4.0 | 7.0 | 7.6 | 7.7 | 8.2 | 7.4 | 8.2 | 7.4 | 8.2 | 5.5 | 1.8 |
| Example 15 | 4.0 | 7.0 | 7.6 | 7.7 | 8.2 | — | 8.0 | 7.4 | 8.0 | 5.6 | 1.8 |
| Example 16 | 4.0 | 7.0 | 7.6 | 7.7 | 8.2 | 7.4 | 8.2 | 7.2 | 8.2 | 5.6 | 1.8 |
| Example 17 | 4.0 | 7.0 | 7.6 | 7.7 | 8.2 | 7.4 | 8.2 | 7.4 | 8.2 | 5.6 | 1.8 |
| Examples 18–23 | 4.0 | 7.0 | 7.6 | 7.7 | 8.2 | 7.2 | — | 7.2 | 8.1 | 5.6 | 1.8 |

TABLE 2

Liquid crystal compounds of general formula (1) and their phase sequences

| Example No. | R | X | Y | m | n | Phase sequences |
|---|---|---|---|---|---|---|
| 1 | 9 | H | F | 2 | 1 | I (114) SCγ* (-7) Cr |
| 2 | 9 | H | F | 0 | 2 | I (104) SCA* (98) Cr |
| 3 | 9 | H | F | 0 | 3 | I (87) SCγ* (58) Cr |
| 4 | 9 | H | F | 1 | 1 | I (118) SA (118) SCA* (85) Cr |
| 5 | 9 | H | F | 1 | 2 | I (96) SC* (90) SCA* (55) Cr |
| 6 | 9 | H | H | 1 | 2 | I (107) SA (102) SC* (91) SCA* (35) Cr |
| 7 | 9 | H | F | 1 | 3 | I (74) SC* (59) SCA* (-21) Cr |
| 8 | 6 | H | F | 2 | 1 | I (134) SA (128) SCγ* (75) SCA* (58) Cr |
| 9 | 7 | H | F | 2 | 1 | I (125) SA (120) SCγ* (48) Cr |
| 10 | 8 | H | F | 2 | 1 | I (121) SA (120) SCγ* (65) SCA* (30) Cr |
| 11 | 10 | H | F | 2 | 1 | I (110) SCγ* (50) SCA* (-9) Cr |
| 12 | 11 | H | F | 2 | 1 | I (104) SCγ* (-8) Cr |
| 13 | 12 | H | F | 2 | 1 | I (102) SA (102) SCγ* (28) Cr |
| 14 | 9 | H | H | 2 | 1 | I (125) SA (119) SCγ* (35) Cr |
| 15 | 9 | F | H | 2 | 1 | I (104) SA (85) SCγ* (47) Cr |
| 16 | 12 | H | H | 2 | 1 | I (106) SA (100) SCγ* (36) Cr |
| 17 | 9 | H | H | 2 | 2 | I (103) SA (98) SCγ* (15) SX (0) Cr |
| 18 | 8 | H | F | 2 | 2 | I (101) SA (101) SCγ*(<-20) Cr |
| 19 | 9 | H | F | 2 | 2 | I (95) SCγ* (<-30) Cr |
| 20 | 9 | H | F | 3 | 1 | I (103) SC* (101) SCA* (26) Cr |
| 21 | 9 | H | F | 3 | 2 | I (84) SCA* (<-20) Cr |
| 22 | 9 | H | F | 4 | 1 | I (96) SCγ* (78) SCA* (-8) Cr |
| 23 | 9 | H | F | 4 | 2 | I (87) SCγ* (<-30) Cr |

In the above table, numerals within the parentheses represent transition temperatures (° C.) in a temperature falling step, I is an isotropic phase, SA is a smectic A phase, SC* is a ferroelectric phase, SCA* is an anti-ferroelectric phase, SCγ* is a ferrielectric phase, SX is an unidentified liquid crystal phase and Cr is a crystal phase.

The ferrielectric liquid crystal compounds obtained in Examples 1, 10, 11, 13 and 14 were examined for optical response. The cell was prepared in the following procedures.

Glass plates with an ITO electrode and an insulating film (SiO$_2$ film as thickness as 50 nm) were coated with polyimide (thickness: about 80 nm) and one of a pair of the glass plates was rubbed. A pair of the glass plates were assembled with a spacer having a particle diameter of 1.6 μm interposed therebetween, to obtain a test cell having a thickness of 2 μm.

The liquid crystals was heated up to a temperature at which the liquid crystal had an isotropic phase, and then injected into the test cell by a capillary phenomenon. Then, the test cell was gradually cooled at a rate of 1° C./min to effect parallel-alignment of the liquid crystal.

When the intensity of transmitted light is minimum, the transmission is defined as 0% and when the intensity is maximum, the transmission is defined as 100%. The phase transition voltage is a voltage at a transmission of 90%.

The test cell was driven by applying a triangle wave voltage of ±10 V and 5 Hz, to obtain a voltage at which the ferrielectric phase is transited to a ferroelectric phase (phase transition voltage I) and a voltage at which the ferroelectric phase is transited to a ferrielectric phase (phase transition voltage II) at the temperatures shown in Table 3.

TABLE 3

Phase transition voltages of ferrielectric liquid crystals

| | Example No. | | | | |
|---|---|---|---|---|---|
| | 1 | 10 | 11 | 13 | 14 |
| Phase transition voltage I (V/μm) | 2.4 | 2.2 | 2.0 | 1.8 | 1.9 |
| Phase transition voltage II (V/μm) | 2.1 | 1.7 | 1.3 | 1.4 | 1.5 |
| Measurement temperature (° C.) | 60 | 110 | 100 | 90 | 109 |

What is claimed is:

1. A liquid crystal compound represented by the following general formula (1):

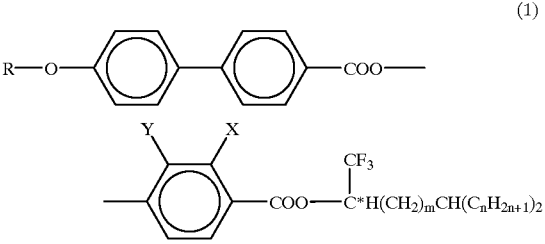

(1)

wherein R is a linear alkyl group having 6 to 12 carbon atoms, X and Y are both a hydrogen atom, or one of them is a hydrogen atom and the other is a fluorine atom, m is an integer of 0 to 5, n is an integer of 1 to 5, and C* is an asymmetric carbon atom.

2. The liquid crystal compound of claim 1, wherein m is an integer of 0 to 4 in the general formula (1).

3. The liquid crystal compound of claim 1, wherein n is an integer of 1 to 3 in the general formula (1).

4. The liquid crystal compound of claim 1, wherein m is 0 in the general formula 1.

5. The liquid crystal compound of claim 4 wherein n is 1 or 2.

6. The liquid crystal compound of claim 1 wherein m is 1 to 3.

7. The liquid crystal compound of claim 6 wherein n is 1 or 2.

* * * * *